United States Patent
Scheibe et al.

(10) Patent No.: US 7,615,044 B2
(45) Date of Patent: Nov. 10, 2009

(54) DEFLECTABLE SHEATH HANDLE ASSEMBLY AND METHOD THEREFOR

(75) Inventors: Grant Alexander Scheibe, Loretto, MN (US); Brian Fischer, Minneapolis, MN (US); Bradley Charles Knippel, Lino Lakes, MN (US); Jeffrey A. Popowski, Roseville, MN (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 11/381,421

(22) Filed: May 3, 2006

(65) Prior Publication Data
US 2007/0260223 A1 Nov. 8, 2007

(51) Int. Cl.
*A61M 25/00* (2006.01)
(52) U.S. Cl. .................. 604/528; 604/95.04; 604/510
(58) Field of Classification Search ............. 604/93.01, 604/95.01, 95.04, 523, 528, 506, 508, 510; 600/433, 434, 435, 585
See application file for complete search history.

(56) References Cited

U.S. PATENT DOCUMENTS

| | | | |
|---|---|---|---|
| 5,030,204 A | 7/1991 | Badger et al. | |
| 5,391,147 A | 2/1995 | Imran et al. | |
| 5,395,329 A | 3/1995 | Fleischhacker et al. | |
| 5,611,777 A | 3/1997 | Bowden et al. | |
| 5,935,102 A | 8/1999 | Bowden et al. | |
| 6,059,739 A | 5/2000 | Baumann | |
| 6,126,654 A * | 10/2000 | Giba et al. | 606/15 |
| 6,132,390 A | 10/2000 | Cookston et al. | |
| 6,394,976 B1 | 5/2002 | Winston et al. | |
| 6,423,059 B1 | 7/2002 | Hanson et al. | |
| 6,491,681 B1 | 12/2002 | Kunis et al. | |
| 6,551,302 B1 * | 4/2003 | Rosinko et al. | 604/505 |
| 6,554,794 B1 | 4/2003 | Mueller et al. | |
| 6,652,506 B2 * | 11/2003 | Bowe et al. | 604/523 |
| 6,805,675 B1 * | 10/2004 | Gardeski et al. | 600/585 |
| 2003/0109861 A1 | 6/2003 | Shimada | |
| 2003/0125663 A1 | 7/2003 | Coleman et al. | |
| 2003/0163085 A1 | 8/2003 | Tanner et al. | |
| 2004/0147828 A1 | 7/2004 | Gibson | |
| 2005/0065467 A1 * | 3/2005 | Pudelko et al. | 604/95.04 |

FOREIGN PATENT DOCUMENTS

WO WO-0067834 A1 11/2000
WO WO-2005081202 A1 9/2005

* cited by examiner

*Primary Examiner*—Kevin C Sirmons
*Assistant Examiner*—Bhisma Mehta
(74) *Attorney, Agent, or Firm*—Michael F. Scalise

(57) ABSTRACT

A deflectable catheter assembly includes a deflectable body manipulatable by a rotating actuator of a housing assembly. The housing assembly includes a sliding member having a threaded portion including a first threaded portion having a first pitch and a second threaded portion having a second pitch, where the first pitch is different than the second pitch.

34 Claims, 6 Drawing Sheets

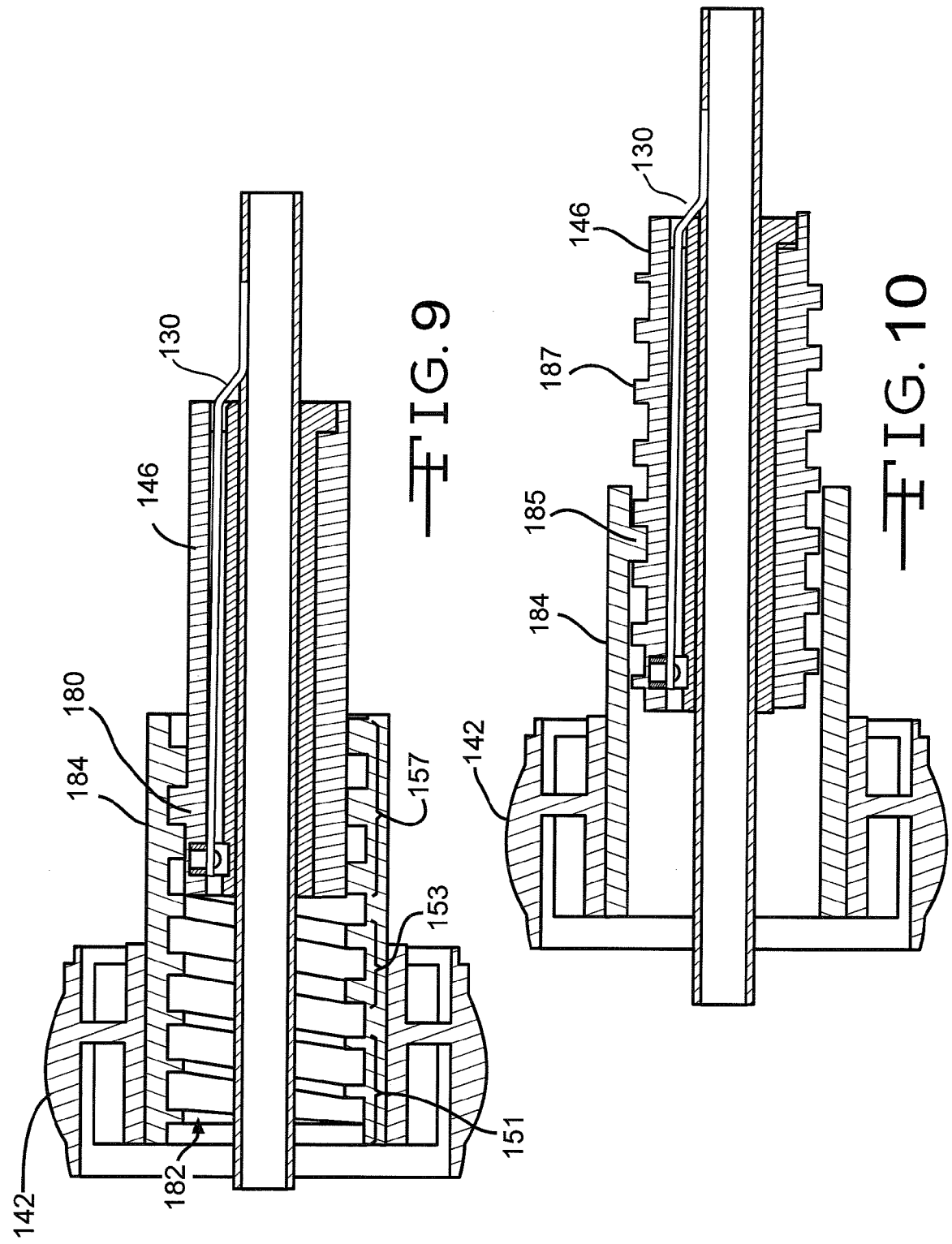

DEFLECTABLE SHEATH HANDLE ASSEMBLY AND METHOD THEREFOR

TECHNICAL FIELD

Deflectable sheath assemblies having deflectable distal ends, and more particularly, a handle assembly for a deflectable sheath assembly.

TECHNICAL BACKGROUND

Medical devices and/or procedures are used in many different branch vessels and require a wide variety in placement techniques. One example of a placement technique is through use of a deflectable sheath. Typically, a deflectable sheath is controlled at a proximal end of the catheter by a control handle that operates a pull wire to deflect the sheath. However, with conventional catheter steering mechanisms, it can be difficult to accurately position the catheters in certain body vessels, such as branch veins. For instance, the mechanisms are awkward or require the use of two hands. Other steering mechanisms require pull wires to be wound and unwound around a rotatable cam wheel, causing increased fatigue on the pull wires, and potentially shortening the life of the device. Furthermore, some deflectable catheters involve relatively large catheter sheaths. The larger sheaths can be difficult to manipulate within a patient, and have increased deflection forces, frustrating efforts of a physician attempting to control deflection angle during a procedure.

SUMMARY OF THE INVENTION

The present invention relates to a deflectable sheath assembly comprising: a deflectable body extending from a distal portion to a proximal portion; a rotatable actuator disposed at the proximal portion of the deflectable body, the rotatable actuator being threadingly engaged with a sliding member such that rotation of the actuator causes longitudinal movement of the sliding member; the sliding member fixedly coupled with a pull wire extending along the deflectable body to the deflectable body distal portion such that pull wire longitudinal movement causes deflection of the deflectable body distal portion; and wherein the rotatable actuator is threadingly engaged with the sliding member through a first threaded portion having a first pitch in co-axial alignment with a second threaded portion having a second pitch that is different than the first pitch, wherein the first and second threaded portions are either part of the rotatable actuator or the sliding member, but not both and wherein the sliding member operablely engages the rotatable actuator with the first threaded portion at a first longitudinal position and with the second threaded portion at a second longitudinal position such that rotation of the actuator causes different rates of translational movement of the sliding member per actuator rotation and consequently different rates of translational movement of the pull wire and further consequently different rates of deflection of the deflectable distal body portion when the sliding member engages the first threaded portion compared to the second threaded portion.

The present invention also relates to a deflectable sheath assembly comprising: a deflectable body extending from a distal portion to a proximal portion, the deflectable body having a passage therethrough; a rotatable actuator disposed at the proximal portion of the deflectable body, the rotatable actuator being threadingly engaged with a sliding member by an intermediate cam such that rotation of the rotatable actuator causes longitudinal translation of the sliding member; wherein the sliding member is fixedly coupled with a pull wire extending along the deflectable body to the deflectable body distal portion; and wherein the cam disposed between the rotatable actuator and the sliding member includes a first threaded cam portion having a first pitch in co-axial alignment with a second threaded cam portion having a second pitch that is different than the first pitch for varying a rate of translation of the sliding member and deflection of the deflectable body distal portion relative to rotation of the rotatable actuator.

The present invention further relates to a method for deflecting the distal portion of a deflectable body of a deflectable sheath assembly, comprising the steps of: providing an actuator of the deflectable sheath assembly, the actuator being threadingly engaged with a sliding member and including a first threaded actuator portion having a first pitch in co-axial alignment with a second threaded actuator portion having a second pitch that is different than the first pitch, the sliding member fixedly coupled with a pull wire that is operably coupled to a distal portion of the deflectable body of the deflectable sheath assembly; rotating the actuator to cause the first threaded portion to engage the sliding member to longitudinally translate the sliding member at a first translational rate per actuator rotation, thereby deflecting the distal portion of the deflectable body at the first rate; and further rotating the actuator to cause the second threaded actuator portion to engage the sliding member to further longitudinally translate the sliding member at a second translational rate per actuator rotation different than the first rate, thereby further deflecting the distal portion of the deflectable body at the second rate different than the first rate.

Still further, the present invention also relates to a deflectable sheath assembly, which comprises: a deflectable body extending from a distal portion to a proximal portion; a rotatable actuator disposed at the proximal portion of the deflectable body and including a pin threadingly engaged with a sliding member, wherein the sliding member comprises a first threaded sliding member portion having a first pitch in co-axial alignment with a second threaded sliding member portion having a second pitch that is different than the first pitch, the sliding member fixedly coupled with a pull wire that is operably coupled to a distal portion of the deflectable body of the deflectable sheath assembly; wherein the pin of the rotatable actuator engages the first threaded sliding member portion to longitudinally translate the sliding member at a first translational rate per actuator rotation, thereby deflecting the distal portion of the deflectable body at the first rate; wherein the pin of the rotatable actuator further engages the second threaded sliding member portion to further longitudinally translate the sliding member at a second translational rate per actuator rotation different than the first rate; and wherein longitudinal translation of the sliding member causes the coupled pull wire to deflect the distal portion of the deflectable body at at least one of the first rate or the second rate different than the first rate.

Moreover, the present invention also relates to a deflectable sheath assembly, which comprises: a deflectable body extending from a distal portion to a proximal portion; a rotatable actuator disposed at the proximal portion of the deflectable body and threadingly engaged with a pin of a sliding member, the rotatable actuator including a first threaded actuator portion having a first pitch in co-axial alignment with a second threaded actuator portion having a second pitch that is different than the first pitch, the sliding member fixedly coupled with a pull wire that is operably coupled to a distal portion of the deflectable body of the deflectable sheath assembly; wherein the pin of the sliding member threadingly engages the first threaded actuator portion to longitudinally translate the sliding member at a first translational rate per actuator rotation, thereby deflecting the distal portion of the deflectable body at the first rate; and wherein the pin of the sliding member further threadingly engages the second threaded actuator portion to further longitudinally translate the sliding member at a second translational rate per actuator rotation different than the first rate; and wherein longitudinal translation of the sliding member causes the coupled pull wire to deflect the distal portion of the deflectable body at at least one of the first rate or the second rate different than the first rate.

Still further, the present invention describes a method for deflecting the distal portion of a deflectable body of a deflectable sheath assembly, comprising the steps of: providing an actuator of the deflectable sheath assembly including a pin threadingly engaged with a sliding member comprising a first threaded sliding member portion having a first pitch in co-axial alignment with a second threaded sliding member portion having a second pitch that is different than the first pitch, wherein the sliding member is fixedly coupled with a pull wire that is operably coupled to a distal portion of the deflectable body of the deflectable sheath assembly; rotating the actuator to cause the pin to engage the first sliding member portion to longitudinally translate the sliding member at a first translational rate per actuator rotation, thereby deflecting the distal portion of the deflectable body at the first rate; and further rotating the actuator to cause the pin to engage the second sliding member portion to further longitudinally translate the sliding member at a second translational rate per actuator rotation different than the first rate, thereby further deflecting the distal portion of the deflectable body at the second rate different than the first rate.

Yet further, the present invention relates to a method for deflecting the distal portion of a deflectable body of a deflectable sheath assembly, comprising the steps of: providing an actuator of the deflectable sheath assembly threadingly engaged with a pin of a sliding member, the actuator including a first threaded actuator portion having a first pitch in co-axial alignment with a second threaded actuator portion having a second pitch that is different than the first pitch, the sliding member being fixedly coupled with a pull wire that is operably coupled to a distal portion of the deflectable body of the deflectable sheath assembly; rotating the actuator to cause the first threaded actuator portion to threadingly engage the pin of the sliding member to longitudinally translate the sliding member at a first translational rate per actuator rotation, thereby deflecting the distal portion of the deflectable body at the first rate; and further rotating the actuator to cause the second threaded actuator portion to threadingly engage the pin of the sliding member to further longitudinally translate the sliding member at a second translational rate per actuator rotation different than the first rate, thereby further deflecting the distal portion of the deflectable body at the second rate different than the first rate.

What is needed is a deflectable catheter that overcomes the shortcomings of previous deflectable catheters. What is further needed is a deflectable catheter that allows for more ease positioning of the distal end of the deflectable catheter, for example for a catheter having a relatively larger sized sheath, and that is usable with a single hand.

BRIEF DESCRIPTION OF THE DRAWINGS

FIG. 9 illustrates a cross-sectional view of a proximal portion of a deflectable catheter assembly as constructed in accordance with at least one embodiment.

FIG. 10 illustrates a cross-sectional view of a proximal portion of a deflectable catheter assembly as constructed in accordance with at least one embodiment.

DESCRIPTION OF THE EMBODIMENTS

In the following detailed description, reference is made to the accompanying drawings, which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the spirit and scope of the present invention. Therefore, the following detailed description is not to be taken in a limiting sense, and the scope is defined by the appended claims.

Figure 1:
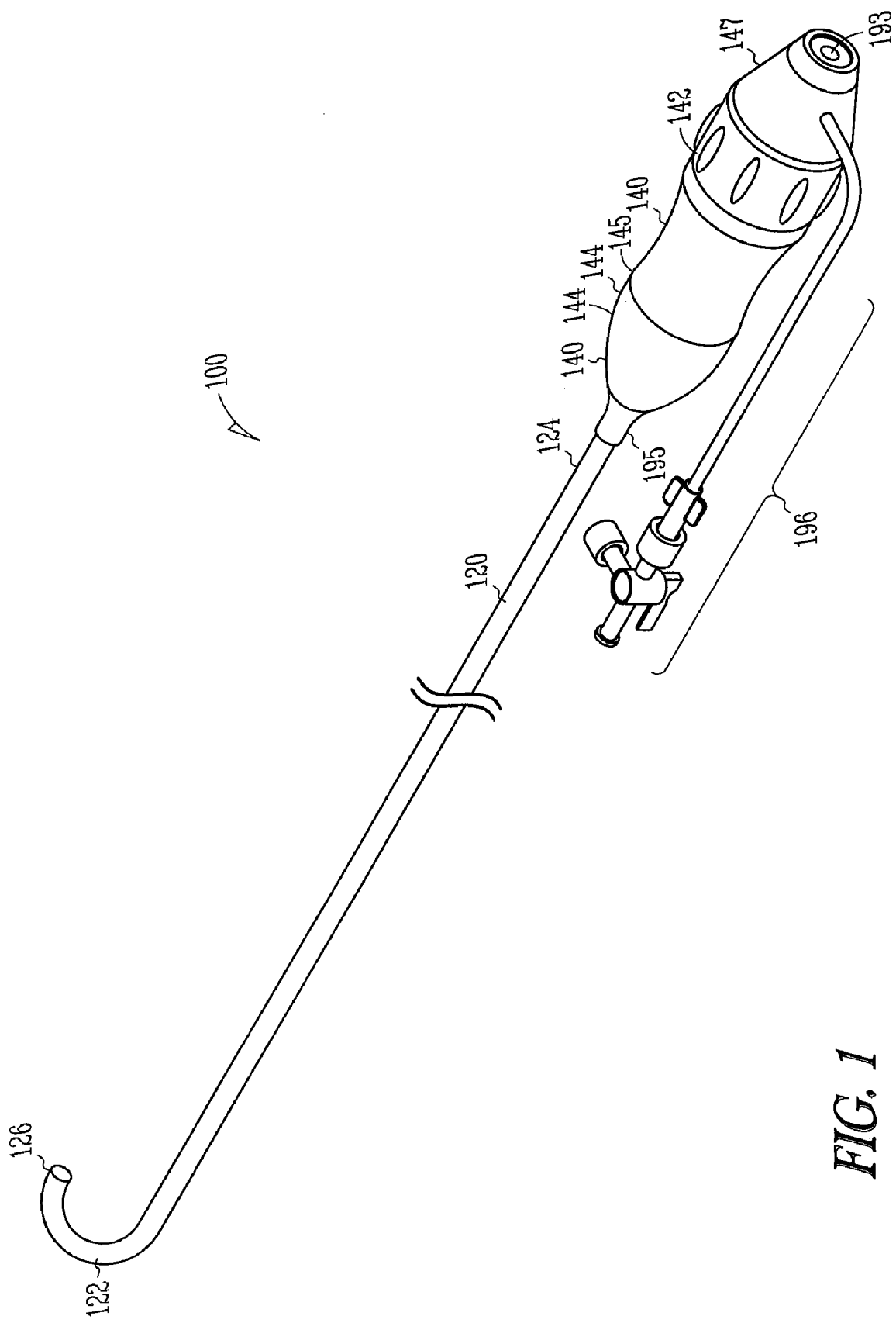
FIG. 1 illustrates a perspective view of a deflectable catheter assembly as constructed in accordance with at least one embodiment.
Figure 2:
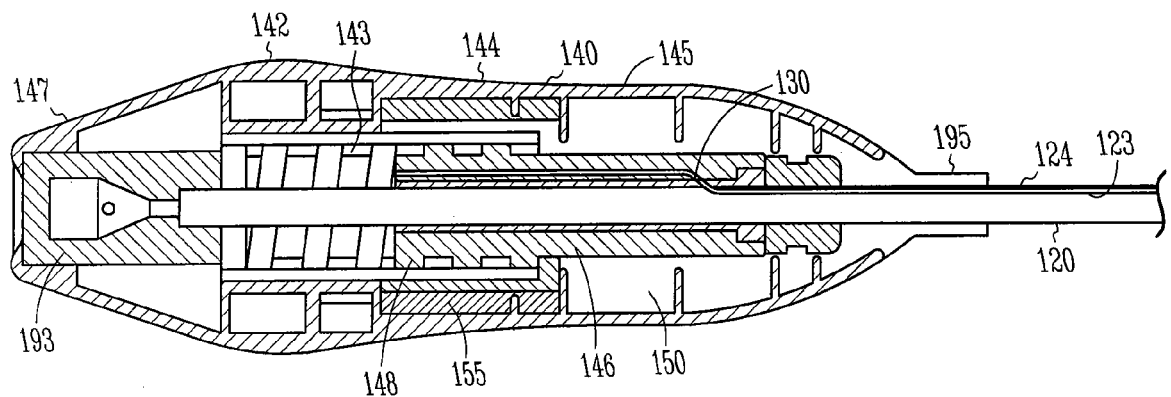
FIG. 2 illustrates a cross-sectional view of a proximal portion of a deflectable catheter assembly as constructed in accordance with at least one embodiment.

A deflectable sheath assembly 100 is illustrated in FIGS. 1 and 2, and generally includes a deflectable body 120, a handle assembly 140, and a pullwire 130. The deflectable body 120 extends from a distal end portion 122 to a proximal end portion 124, and includes a passage 123 therethrough. The passage 123 allows for instruments to be introduced through the sheath assembly 100 and into the patient. Near the distal end portion 122 is a deflectable distal tip 126 that is, in an option, more flexible than the remainder of the deflectable body 120.

Near the deflectable distal tip 126, a distal portion of the pullwire 130 (FIG. 2) is coupled with the deflectable body 120. For example, the pullwire 130 (FIG. 2), in an option, is fixed to the deflectable body 120 at a distal end of the distal tip 126. In another option, the pullwire 130 is fixed to the deflectable body 120 with a pullwire anchor.

The pullwire 130 is disposed through a lumen of the deflectable body 120, and translates longitudinally through the lumen. A proximal portion of the pullwire 130 is coupled with a portion of the handle assembly 140. As the pullwire 130 is moved longitudinally through the lumen of the deflectable body 120, the pullwire 130, which is fixed to the distal portion of the deflectable body 120, deflects the distal end portion 122 of the deflectable body 120.

The proximal end portion 124 of the deflectable body 120 is fixed to the handle assembly 140 and assists a user in manipulation of the distal end portion deflectable body 120. The handle assembly 140 allows for the user to displace the pullwire 130 relative to the deflectable body 120 with an actuator, for example, by a rotating knob 142.

Disposed near the proximal end portion 124 of the deflectable body 120 is a flexible strain relief 195, as illustrated in FIGS. 1 and 2. The strain relief 195 is available in different sizes to accommodate different sheath diameters, for example deflectable bodies 120. The strain relief 195 is made from a flexible material to allow it to flex with the deflectable body 120. The integrated strain relief 195 assists in preventing the deflectable body 120 from kinking near the handle assembly 140 by maintaining a minimum bend radius. The stiffness of the strain relief 195 decreases over the length of the strain relief 195, with the proximal end being stiffer than the distal end. The change in stiffness provides a smooth transition from the rigid handle assembly 140 to the flexible deflectable body 120.

The handle assembly 140, shown in greater detail in FIGS. 2 and 9, includes a housing 144 that houses several components therein. The housing 144 includes handle body 145 and a rear cap 147, where the knob 142 separates the handle body 145 from the rear cap 147. Within the housing 144 is a sliding member 146 that interacts with the rotating knob 142, and the sliding member 146 moves longitudinally within the handle assembly 140. In an option, the sliding member 146 includes a threaded portion 148 that is threadingly engaged with internal threads 143 of the rotating knob 142, or a cam 184 coupled with the rotating knob 142.

As illustrated in FIG. 9, the threaded portion 182, in an option, includes a first threaded portion 151 and a second threaded portion 153, where the second threaded portion 153 is more distal than the first threaded portion 151. The first threaded portion 151 has a different pitch than the second threaded portion. In an option, the first threaded portion 151 has a finer pitch than the second threaded portion 153. In a further option, the threaded portion 182 includes a third threaded portion 157 having a different pitch than at least one of the first or second threaded portions. In an example, the first threaded portion 151 differs from the second threaded portion 153 by about 16%. For instance, an example includes the first threaded portion 151 having a pitch of 0.250 in/rev, and the second threaded portion 153 having a pitch of 0.300 in/rev. In another example, the first threaded portion 151 has a pitch of 0.200 in/rev, and the second threaded portion 153 having a pitch of 0.250 in/rev. In a further example, a third threaded portion has a pitch that is about 16% different than the second threaded portion, and the second threaded portion has a pitch that is about 16% different than the first threaded portion. In an example, the first threaded portion has a pitch of about 0.200 in/rev, the second threaded portion has a pitch of about 0.250 in/rev, and the third threaded portion has a pitch of about 0.300 in/rev.

It should be noted that a gradual change in pitch is possible, or several discrete different threaded portions are possible. This allows for greater control of the deflection of the distal end of the catheter assembly when the deflectable body becomes more deflected. The pitch of the threaded portion is varied along the sliding member 146 such that the rate of translation of the sliding member 146 varies relative to rotation of the actuator. In a further option, the pitch of the threaded portion includes square threads. The sliding member 146 further includes features that mate with a support, further discussed below.

Figure 7:
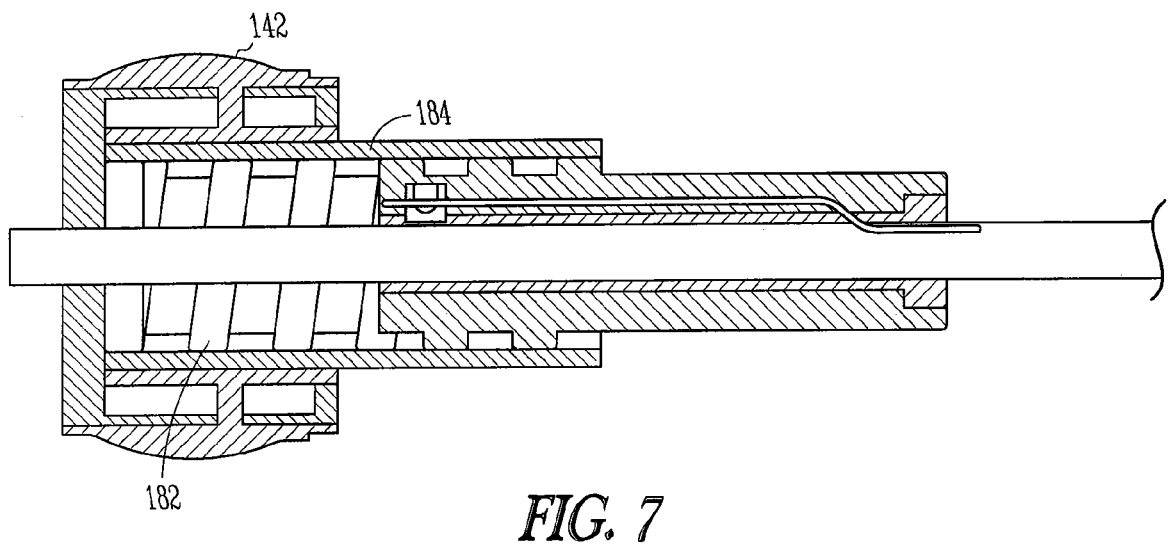
FIG. 7 illustrates a cross-sectional view of a proximal portion of a deflectable catheter assembly as constructed in accordance with at least one embodiment.
Figure 8:
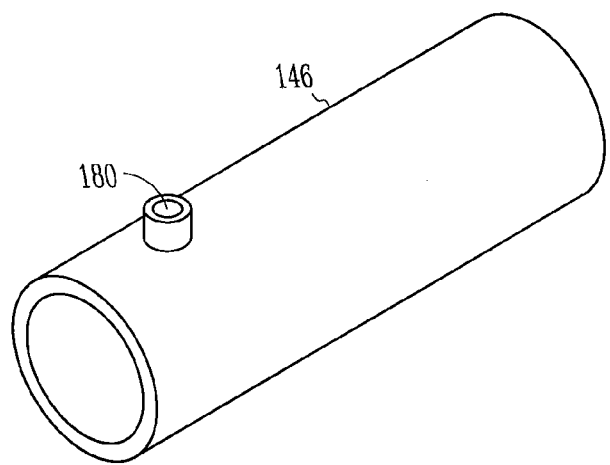
FIG. 8 illustrates a perspective view of a cam of a deflectable catheter assembly as constructed in accordance with at least one embodiment.

Further options for the sliding member 146 include, but are not limited to, embodiments shown in FIGS. 7-10. In FIGS. 7, 8, and 9, the sliding member 146 includes a projection, such as a pin 180. The pin 180 is engaged with an internal threaded portion 182 of a cam 184. The cam 184 is fixed to the rotating knob 142. In an option, the threaded portion 182 has a constant thread. In another option, the threaded portion 182 includes a varying pitch. As the knob is rotated, the threads of the cam 184 engage with the pin 180, and translate the sliding member 146 longitudinally to deflect the distal end portion of the deflectable body 120. Referring to FIG. 10, the internal threaded portion 182 and pin 180 can be reversed as shown in such that the cam 184 has an internal pin 185 and the sliding member 146 has an external thread 187. It should be noted that the external thread 187 can have a variable pitch, and other threaded portions can be varied to achieve the affect of having a variable pitch.

Further included within the handle assembly 140 are a first bearing 155 and an optional second bearing 150. In an option, the first bearing 155 has a larger inner diameter than the second bearing 150. In an option, the first and second bearings 155, 150 are coupled with the handle body 145 and are disposed around the sliding member 146. The first bearing 155 allows for rotation of the knob 142 while controlling the position of the knob 142 both radial and axially. The second bearing 150 allows for the sliding member 146 to slide axially while controlling its position radially.

Figure 3:
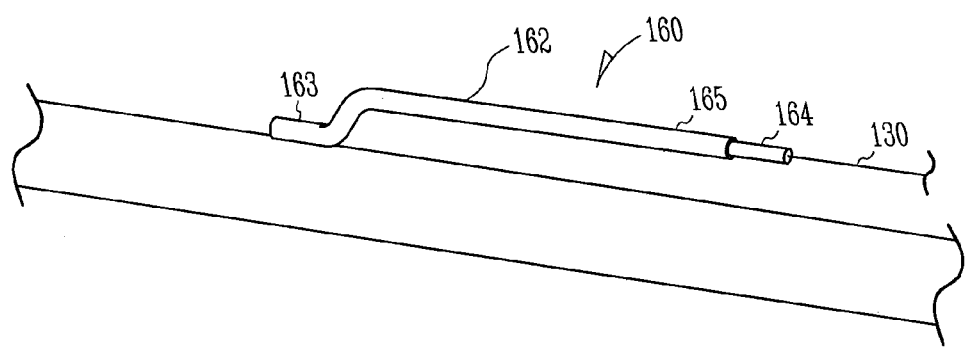
FIG. 3 illustrates a perspective view of a portion of a deflectable catheter assembly as constructed in accordance with at least one embodiment.

The handle assembly 140 further includes a plurality of telescoping tubes 160, such as hypotubes, as illustrated in FIGS. 2 and 3. The telescoping tubes 160 provide support to the pullwire 130 such that it can be loaded in tension and compression without buckling. In an option, the telescoping tubes include a first outer tube 162, such as a curved, outer hypotube. The tubes 160 also include a second inner tube 164, such as a relatively smaller, substantially straight inner hypotube. The first outer tube 162 is fixedly coupled with another component. For example, the first outer tube 162 is embedded in the wall of the deflectable body 120 near the proximal end portion 124, for instance at the location where the pullwire 130 exits the wall of the body 120. The lumen inside the body 120 wall containing the pullwire 130 extends into the outer tube 162.

Referring to FIGS. 2 and 3, the lumen terminates inside the outer tube 162 at a distal end 163 of the outer tube 162. The inner tube 164 fits into a proximal end 165 of the outer tube 162. The inner tube 164 is axially movably relative to the outer tube 162, for example the inner tube 164 telescopes within the outer tube 162. The pullwire 130 is disposed through the lumen in the wall of the deflectable body 120, into the outer tube 162, through the outer tube 162 and into the inner tube 164. The pullwire 130 terminates at the proximal end of the inner tube 164. The pullwire 130 is fixed to the inner tube 164 but is allowed to slide freely inside the outer tube 162. The inner tube 164 is fixed to the sliding member 146.

Figure 4A:
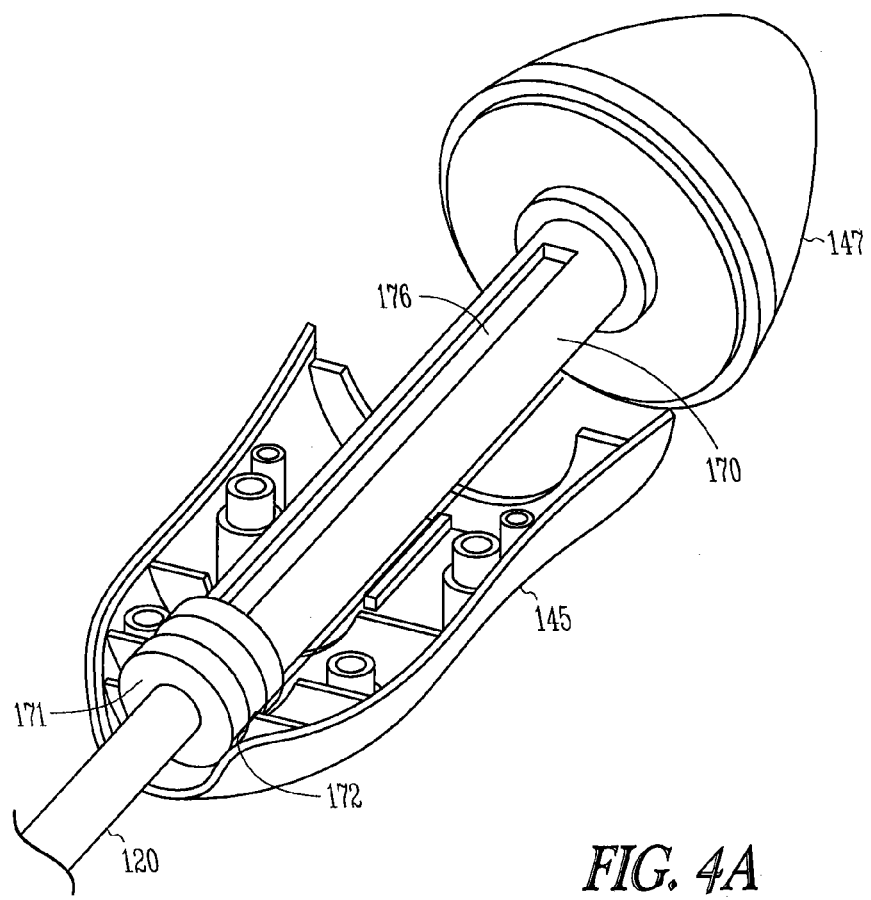
FIG. 4A illustrates a view of a portion of a deflectable catheter assembly as constructed in accordance with at least one embodiment.
Figure 4B:
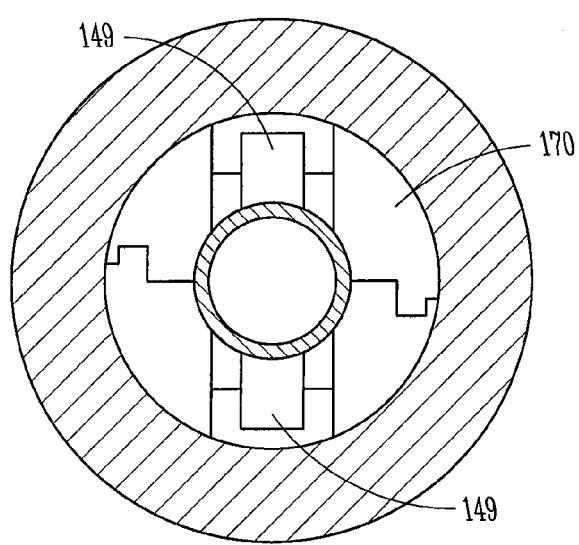
FIG. 4B illustrates a cross-sectional view of a proximal portion of a deflectable catheter assembly as constructed in accordance with at least one embodiment.
Figure 5:
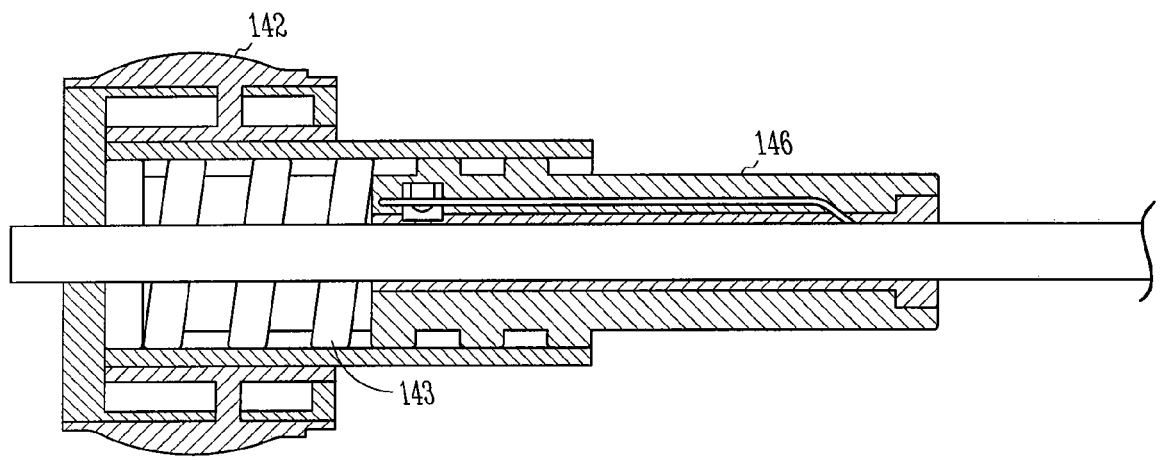
FIG. 5 illustrates a cross-sectional view of a proximal portion of a deflectable catheter assembly as constructed in accordance with at least one embodiment.
Figure 6:
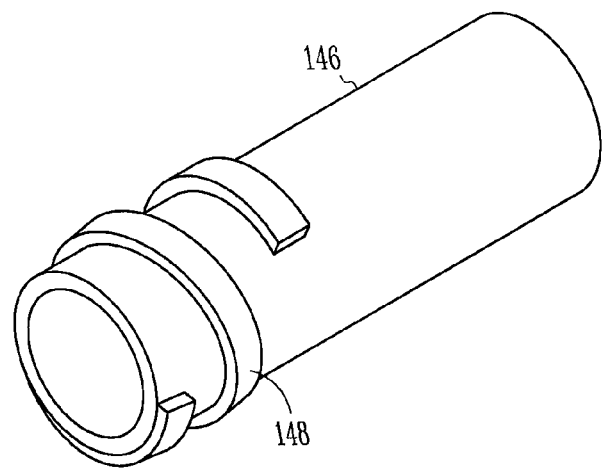
FIG. 6 illustrates a perspective view of a lead screw of a deflectable catheter assembly as constructed in accordance with at least one embodiment.

Referring to FIGS. 4A and 4B, handle body 145 has one or more supports 170 therein. For example, the one or more supports 170 can be integrated with the handle body 145 or the deflectable body 120, and provide reinforcement to the deflectable body 120. In another example, the one or more supports 170 are independent components fixed between the deflectable body 120 and the handle body 145. The one or more supports 170 position the deflectable body 120 within the handle body 145, and in an option have features that mate with features inside the handle body 145. In one example, the one or more supports 170 include a generally annular shape 171 that mates with pockets 172 of the handle body 145. These features hold the one or more supports 170, and the deflectable body 120, in a fixed position within the handle body 145.

The one or more supports 170 further include features that mate with the sliding member 146, and prevent the sliding member 146 from rotating as it slides when the actuator is rotated. The features provide a guide for the sliding member 146 to travel as it slides. For example, the one or more supports 170 includes one or more channels 176 that engage a projection 149 from the sliding member 146, and the projection 149 of the sliding member 146 travels along the guide channels 176. The projection 149 and/or channels 176 can have a variety of cross-sectional shapes. In another option, the projection 149 can be disposed along the one or more supports 170, and the channels 176 can be disposed along the sliding member 146.

In another option, the one or more supports 170 further include features that mate with the end cap of the housing assembly. For example, the one or more supports 170 provide a backbone through the center of the handle assembly, and a proximal end of the one or more supports 170 is fixed to the rear cap 147 of the handle assembly 140. This allows for the entire rotating knob to be exposed around its perimeter, allowing a user to access the knob in any orientation.

Referring again to FIG. 1, the handle assembly 140, in an example, the end cap, includes either a hemostasis valve 193 with flushport assembly 196 or luer fitting at the proximal end of the handle assembly. The hemostasis valve is sealingly engaged with the passage 123 and allows devices of various sizes to be passed into and through the deflectable sheath assembly while protecting against blood loss and air embolism. The flushport assembly 196 allows the sheath assembly 100 to be flushed to remove air. The flushport assembly 196 also allows various fluids to be injected through the sheath assembly 100 during a medical procedure. The luer fitting allows a variety of external components with a mating luer fitting to be attached to the proximal end of the sheath assembly 100. The luer fitting allows other devices to be passed into and through the passage of the deflectable sheath.

During use of the deflectable sheath assembly 100, the distal end portion of the deflectable body 120 is introduced into a patient. The assembly 100 is navigated through the patient, for example, by deflecting the distal end portion of the deflectable body 120. To deflect the distal end portion of the deflectable 120, the actuator is rotated. As the actuator is rotated, the threads of the actuator or the cam engage the threads or a projection of the sliding member 146. The actuator is fixed longitudinally, causing the sliding member 146 to translate longitudinally as the threads enmesh with each other. The sliding member 146, in an option, slides along a guide of a support. For instance, a projection of the sliding member slides along a recess or channel within a support member.

As the sliding member translates longitudinally, in an option, the rate of longitudinal movement of the slider is varied relative to rotation of the actuator. For example, the sliding member includes two or more threaded portions have at least a first pitch and a second pitch, and the actuator is rotated along the first pitch and the second pitch, and the first pitch is different than the second pitch. In another example, varying the rate of longitudinal movement of the sliding member 146 includes decreasing the longitudinal movement of the slider relative the rotation of the actuator.

The sliding member 146 is fixed to an inner tube 164 and moves axially when the knob is rotated. The inner tube 164 is fixed to the pullwire, causing the pullwire to translate longitudinally along the deflectable body 120. The inner tube 164 telescopes within the outer tube 162 during the longitudinal movement.

In an example, when the knob is rotated clockwise (as viewed from the proximal end of the handle) by the user, the sliding member 146 moves proximally and the inner tube 164 slides proximally but stays inside the outer tube. The pullwire is fixed to the inner tube 164, the proximal movement loads the pullwire in tension and also the pullwire longitudinally moves toward a proximal end of the deflectable sheath assembly. The proximal movement of the pullwire causes the distal tip of the sheath to deflect. Conversely, when the knob is rotated counterclockwise, the sliding member 146 moves distally and the inner tube 164 slides distally. This places the pullwire in compression, and the pullwire longitudinally moves toward a distal end of the deflectable sheath assembly. The movement toward the distal end causes the distal tip to straighten.

Advantageously, the sheath assembly allows for improved mechanical advantage in deflecting sheaths having relatively greater deflection forces, such as larger diameter sheaths, sheaths having greater wall thicknesses, or sheaths having reinforcement materials therein. For example, the variable pitch threaded assists in increasing the amount of mechanical advantage as deflection angle and force increase. This assists in maintaining a constant user input throughout the deflection angle. The sheath assembly further assists the user in manipulating the sheath assembly allowing for single-handed operation.

It is to be understood that the above description is intended to be illustrative, and not restrictive. Although the use of the implantable device has been described for use as a lead in, for example, a cardiac stimulation system, the implantable device could as well be applied to other types of body stimulating systems. Many other embodiments will be apparent to those of skill in the art upon reviewing the above description. The scope should, therefore, be determined with reference to the appended claims, along with the full scope of equivalents to which such claims are entitled.

What is claimed is:

1. A deflectable sheath assembly comprising:
   a) a deflectable body extending from a distal portion to a proximal portion;
   b) a rotatable actuator disposed at the proximal portion of the deflectable body, the rotatable actuator being threadingly engaged with a sliding member such that rotation of the actuator causes longitudinal movement of the sliding member;
   c) the sliding member fixedly coupled with a pull wire extending along the deflectable body to the deflectable body distal portion such that pull wire longitudinal movement causes deflection of the deflectable body distal portion; and
   d) wherein the rotatable actuator is threadingly engaged with the sliding member through a first threaded portion having a first pitch in co-axial alignment with a second threaded portion having a second pitch that is different than the first pitch, wherein the first and second threaded portions are either part of the rotatable actuator or part of the sliding member, but not both of them and wherein the sliding member operablely engages the rotatable actuator with the first threaded portion at a first longitudinal position and with the second threaded portion at a second longitudinal position such that rotation of the actuator causes different rates of translational movement of the sliding member per actuator rotation and consequently different rates of translational movement of the pull wire and further consequently different rates of deflection of the deflectable distal body portion when the sliding member engages the first threaded portion compared to the second threaded portion.

2. The deflectable sheath assembly as recited in claim 1, wherein the second pitch is disposed distal to the first pitch.

3. The deflectable sheath assembly as recited in claim 1, wherein the rotatable actuator further comprises a third threaded portion having a third pitch, and wherein the third pitch is different than at least one of the first pitch or the second pitch.

4. The deflectable sheath assembly as recited in claim 1, wherein at least one of the first or the second threaded portions includes generally square teeth.

5. The deflectable sheath assembly as recited in claim 1, further comprising at least one support member coupled with the deflectable body and a housing disposed at the proximal portion of the deflectable body.

6. The deflectable sheath assembly as recited in claim 5, wherein the at least one support member is coupled with the housing within a recess in the housing.

7. The deflectable sheath assembly as recited in claim 1, further comprising telescoping members disposed over the pull wire.

8. The deflectable sheath assembly as recited in claim 1, further comprising a guide, and the sliding member moves along the guide.

9. The deflectable catheter assembly as recited in claim 1 wherein the second pitch is greater than the first pitch.

10. A deflectable sheath assembly comprising:
a) a deflectable body extending from a distal portion to a proximal portion, the deflectable body having a passage therethrough;
b) a rotatable actuator disposed at the proximal portion of the deflectable body, the rotatable actuator being threadingly engaged with a sliding member by an intermediate cam such that rotation of the rotatable actuator causes longitudinal translation of the sliding member;
c) wherein the sliding member is fixedly coupled with a pull wire extending along the deflectable body to the deflectable body distal portion; and
d) wherein the cam disposed between the rotatable actuator and the sliding member includes a first threaded cam portion having a first pitch in co-axial alignment with a second threaded cam portion having a second pitch that is different than the first pitch for varying a rate of translation of the sliding member and deflection of the deflectable body distal portion relative to rotation of the rotatable actuator.

11. The deflectable sheath assembly as recited in claim 10, further comprising a hemostatic valve sealingly engaged with the passage.

12. The deflectable sheath assembly as recited in claim 10, wherein the first pitch is finer than the second pitch.

13. The deflectable sheath assembly as recited in claim 10, wherein at least one of the first threaded portion or the second threaded portion includes generally square teeth.

14. The deflectable sheath assembly as recited in claim 10, further comprising at least one support coupled with the deflectable body and a housing disposed at the proximal portion of the deflectable body.

15. The deflectable sheath assembly as recited in claim 14, wherein the at least one support is coupled with the housing within a recess in the housing.

16. A method for deflecting the distal portion of a deflectable body of a deflectable sheath assembly, comprising the steps of:
a) providing an actuator of the deflectable sheath assembly, the actuator being threadingly engaged with a sliding member and including a first threaded actuator portion having a first pitch in coaxial alignment with a second threaded actuator portion having a second pitch that is different than the first pitch, the sliding member fixedly coupled with a pull wire that is operably coupled to a distal portion of the deflectable body of the deflectable sheath assembly;
b) rotating the actuator to cause the first threaded portion to engage the sliding member to longitudinally translate the sliding member at a first translational rate per actuator rotation, thereby deflecting the distal portion of the deflectable body at the first rate; and
c) further rotating the actuator to cause the second threaded actuator portion to engage the sliding member to further longitudinally translate the sliding member at a second translational rate per actuator rotation different than the first rate, thereby further deflecting the distal portion of the deflectable body at the second rate different than the first rate.

17. The method as recited in claim 16, including providing the first translational rate per actuator rotation resulting from the first pitch being less than the second translational rate per actuator rotation resulting from the second pitch.

18. The method as recited in claim 16, including providing telescoping members over the pull wire as the distal portion deflects.

19. The method as recited in claim 16, including providing the second translational rate per actuator rotation being less than the first translational rate per actuator rotation.

20. The method as recited in claim 16, wherein translating the sliding member includes sliding a projection along a recess.

21. The method of claim 16 including providing the actuator comprising a cam that is threadingly engaged with the sliding member, the cam including the first threaded actuator portion having the first pitch in co-axial alignment with the second threaded actuator portion having the second pitch that is different than the first pitch.

22. The method of claim 16 including providing the second pitch being disposed distal to the first pitch.

23. A deflectable sheath assembly, which comprises:
a) a deflectable body extending from a distal portion to a proximal portion;
b) a rotatable actuator disposed at the proximal portion of the deflectable body and including a pin threadingly engaged with a sliding member, wherein the sliding member comprises a first threaded sliding member portion having a first pitch in co-axial alignment with a second threaded sliding member portion having a second pitch that is different than the first pitch, the sliding member fixedly coupled with a pull wire that is operably coupled to a distal portion of the deflectable body of the deflectable sheath assembly;
c) wherein the pin of the rotatable actuator engages the first threaded sliding member portion to longitudinally translate the sliding member at a first translational rate per actuator rotation, thereby deflecting the distal portion of the deflectable body at the first rate;
d) wherein the pin of the rotatable actuator further engages the second threaded sliding member portion to further longitudinally translate the sliding member at a second translational rate per actuator rotation different than the first rate; and e) wherein longitudinal translation of the sliding member causes the coupled pull wire to deflect the distal portion of the deflectable body at at least one of the first rate or the second rate different than the first rate.

24. The deflectable sheath assembly of claim 23 wherein the second pitch is disposed distal to the first pitch, and the second pitch is greater than the first pitch.

25. The deflectable sheath assembly of claim 23 wherein the second pitch is greater than the first pitch.

26. A deflectable sheath assembly, which comprises:

a) a deflectable body extending from a distal portion to a proximal portion;

b) a rotatable actuator disposed at the proximal portion of the deflectable body and threadingly engaged with a pin of a sliding member, the rotatable actuator including a first threaded actuator portion having a first pitch in co-axial alignment with a second threaded actuator portion having a second pitch that is different than the first pitch, the sliding member fixedly coupled with a pull wire that is operably coupled to a distal portion of the deflectable body of the deflectable sheath assembly;

c) wherein the pin of the sliding member threadingly engages the first threaded actuator portion to longitudinally translate the sliding member at a first translational rate per actuator rotation, thereby deflecting the distal portion of the deflectable body at the first rate; and d) wherein the pin of the sliding member further threadingly engages the second threaded actuator portion to further longitudinally translate the sliding member at a second translational rate per actuator rotation different than the first rate; and e) wherein longitudinal translation of the sliding member causes the coupled pull wire to deflect the distal portion of the deflectable body at at least one of the first rate or the second rate different than the first rate.

27. The deflectable sheath assembly of claim 26 wherein the second pitch is disposed distal to the first pitch.

28. The deflectable sheath assembly of claim 26 wherein the second pitch is greater than the first pitch.

29. A method for deflecting the distal portion of a deflectable body of a deflectable sheath assembly, comprising the steps of:

a) providing an actuator of the deflectable sheath assembly including a pin threadingly engaged with a sliding member comprising a first threaded sliding member portion having a first pitch in co-axial alignment with a second threaded sliding member portion having a second pitch that is different than the first pitch, wherein the sliding member is fixedly coupled with a pull wire that is operably coupled to a distal portion of the deflectable body of the deflectable sheath assembly;

b) rotating the actuator to cause the pin to engage the first sliding member portion to longitudinally translate the sliding, member at a first translational rate per actuator rotation, thereby deflecting the distal portion of the deflectable body at the first rate; and c) further rotating the actuator to cause the pin to engage the second sliding member portion to further longitudinally translate the sliding member at a second translational rate per actuator rotation different than the first rate, thereby further deflecting the distal portion of the deflectable body at the second rate different than the first rate.

30. The method of claim 29 including providing the second pitch being disposed distal to the first pitch.

31. The method of claim 29 including providing the second pitch being greater than the first pitch.

32. A method for deflecting the distal portion of a deflectable body of a deflectable sheath assembly, comprising the steps of:

a) providing an actuator of the deflectable sheath assembly threadingly engaged with a pin of a sliding member, the actuator including a first threaded actuator portion having a first pitch in co-axial alignment with a second threaded actuator portion having a second pitch that is different than the first pitch, the sliding member being fixedly coupled with a pull wire that is operably coupled to a distal portion of the deflectable body of the deflectable sheath assembly;

b) rotating the actuator to cause the first threaded actuator portion to threadingly engage the pin of the sliding member to longitudinally translate the sliding member at a first translational rate per actuator rotation, thereby deflecting the distal portion of the deflectable body at the first rate; and c) further rotating the actuator to cause the second threaded actuator portion to threadingly engage the pin of the sliding member to further longitudinally translate the sliding member at a second translational rate per actuator rotation different than the first rate, thereby further deflecting the distal portion of the deflectable body at the second rate different than the first rate.

33. The method of claim 32 including providing the second pitch being disposed distal to the first pitch.

34. The method of claim 32 including providing the second pitch being greater than the first pitch.

* * * * *